United States Patent [19]

McMullen et al.

[11] 4,138,290

[45] Feb. 6, 1979

[54] GLUCOSE ISOMERIZATION UNDER EXPANDED BED CONDITIONS

[75] Inventors: William H. McMullen, Norwalk, Conn.; William Carasik, Ridgewood, N.J.

[73] Assignee: Novo Laboratories, Incorporated, Wilton, Conn.

[21] Appl. No.: 679,445

[22] Filed: Apr. 22, 1976

[51] Int. Cl.$^2$ ............................................. C12D 13/02
[52] U.S. Cl. .................................... 195/31 F; 195/63; 195/68; 195/DIG. 11; 195/115
[58] Field of Search ..................... 195/65, 63, 68, 115, 195/31 F, 116, DIG. 11

[56] References Cited

U.S. PATENT DOCUMENTS

| | | | |
|---|---|---|---|
| 3,821,086 | 6/1974 | Lee et al. | 195/116 |
| 3,928,143 | 12/1975 | Coughlin | 195/115 |
| 3,960,663 | 6/1976 | Tamura et al. | 195/31 F |
| 3,980,521 | 9/1976 | Amotz et al. | 195/63 |

OTHER PUBLICATIONS

Emery et al., "Some Applications of Solid-Phase Enzymes in Biological Engineering", Birmingham Univ. Chem. Engineer, vol. 22, No. 2, (Summer 1971), pp. 37-41.

Barker et al., "Enzyme Reactors for Industry", Process Biochemistry, vol. 6, No. 10 (Oct. 1971), pp. 11-13.

Primary Examiner—Raymond N. Jones
Assistant Examiner—Thomas G. Wiseman
Attorney, Agent, or Firm—Fidelman, Wolffe & Waldron

[57] ABSTRACT

Expanded bed isomerization of glucose syrup to a glucose-fructose mixture having a fructose proportion exceeding about 40% of the glucose-fructose content by passing 30-55% w/w of glucose syrup through a cell-mass glucose isomerase preparation in the form of a bed of uniform particles of controlled size in the range of 150-2000 micrometers at a superficial syrup velocity of 0.5-15 meters an hour. Velocity and particle size are inversely related to create bed expansion within the range of 5-100%.

Bed life may be extended by substituting fresh catalyst for inactivated catalyst.

The isomerase should have an activity exceeding about 100 IGIC u/gm.

The isomerase should be weighted by incorporation therein of finely divided alumina particles.

5 Claims, No Drawings

GLUCOSE ISOMERIZATION UNDER EXPANDED BED CONDITIONS

BACKGROUND OF THE INVENTION

The present invention relates to a method for carrying out isomerization of glucose under expanded bed conditions.

Glucose syrup prepared by enzymatically liquefying and dextrinizing an aqueous (corn) starch suspension, the dextrin thereafter being enzymatically saccharified, may be enzymatically isomerized into a glucose-fructose mixture syrup by contacting the glucose syrup with a microorganism derived glucose isomerase preparation using reaction conditions such as pH temperature enzyme concentrations, contact time, etc. which achieve an optimum conversion to a glucose-fructose mixture reasonably approximating 50:50 glucose-fructose. High fructose syrups are sweeter than glucose syrups, and have been substituted widely for sucrose (i.e. cane and beet sugar syrup).

As the high fructose syrup art developed into a large scale industry workers in the art became interested in adopting long standing process design principles, including for example the possibilities of carrying out the isomerization of glucose syrups under fluidized bed conditions. U.S. Pat. No. 3,928,143 describes in some detail the desirability of carrying out enzyme catalyzed reactions with an expanded bed of enzyme catalyst particles and approximately plug flow for the fluid.

Glucose isomerase is normally an intracellular enzyme, and this enzyme as initially produced is simply a collected mass of microorganism cells. Processing the cells to liberate a pure enzyme then bonding such an enzyme to the dense particle required for the process described in U.S. Pat. No. 3,928,143 makes the enzyme coated dense particle relatively expensive. Manifestly conversion of the cell mass itself into fluidizable particles would offer substantial cost advantages.

An object of this invention is to provide a cell mass glucose isomerase preparation in fluidizable particle form.

A further object of this invention is to provide an expanded bed procedure for carrying out isomerization of glucose.

Conversion of the individual glucose isomerase containing microorganism cells into reusable relatively large particles has been accomplished by prior workers in the art, availability of such an enzyme form being a major prerequisite for fluidized bed isomerization. Reference is made to U.S. Pat. No. 3,821,086 and to pending U.S. application Ser. No. 501,292 filed Aug. 28, 1974, now U.S. Pat. No. 3,980,521 for the details of quite diverse methods for converting glucose isomerase microorganism cells into cell mass particulate form. The terms cell mass particles, and cell mass particulate form are intended to refer to particles formed or fabricated from the substance of the microorganism cells and organic reactants such as glutaraldehyde, proteins, or agglomerating agents e.g. polyelectrolytes.

However, a specific disadvantage of cell mass particles is their relatively low density. Necessarily the particles fall within the density range of biologically derived substances. For example the true density of enzyme particles made according to the preferred practice described in Ser. No. 501,292 is about 1.4g/ml. For expanded bed purposes such low density enzyme preparations constitute so significant a disadvantage as to raise doubt whether isomerization under expanded bed conditions is feasible with cell mass particulate form enzymes.

It has however, been determined that glucose isomerization can be carried out successfully under expanded bed conditions with cell mass particulate enzyme preparations.

THE INVENTION

Briefly stated, glucose to fructose conversion, in excessive of 40% conversion and treatment of concentrated glucose syrups (30-55% weight-weight) can be carried out enzymatically under expanded bed conditions if the cell mass particulate enzyme preparation is of controlled particle size (wet) in the range of about 150-2,500 microns and the particle size is uniform (insofar as is reasonably possible). The enzyme particles should have approximately the same size in all three dimensions and be ±30% of the mean diameter. The superficial flow rate of the glucose syrup must be kept within the relatively low level range of 0.5-15 meters per hour. The particle size and flow rate are related so that the bed expansion will be relatively low, i.e. 5-100% bed expansion. In addition the activity of the enzyme preparation should be reasonably high, i.e. exceeding about 100 IGIC U/gram.

For one preferred mode of enzyme preparation the following empirical equation has provided a reasonable degree of predictability (for experiment purposes and plant design purposes).

$$E = -130.606 - 40.962\,P - 0.502\,T + 4.470\,S + 11.084\,V$$

where
$E$ = % bed expansion
$P$ = particle size (mm)
$T$ = reactor temperature (° C.)
$S$ = percent solids (w/w) in substrate
$V$ = superficial linear velocity (meters/hour)

A preferred mode of particle is formed when finely divided alumina is incorporated into the cell mass particle, uniformly distributed therein the alumina amounting to 5-20% of the particle weight. Presence of the alumina increases particle density (e.g. to 1.5 g/ml) which improves the fluidization characteristics of the particles.

RATIONALE OF THE INVENTION

An important requirement for an expanded bed enzymatic isomerization is that syrup flow through the expanded bed of enzyme particles must approach plug flow very closely. Back mixing of the syrup is particularly detrimental, because the glucose-fructose syrup product desired by the art is near to the theoretical equilibrium for enzymatic isomerization of glucose and back mixing results in lower fructose content. The art has encountered far too much difficulty in exceeding 40% fructose (on a dry solids basis) to accept the lower fructose content product obtainable without plug flow through an expanded bed reactor.

Two related specific conditions to be avoided are channeling and top to bottom solids migration. Channeling can be prevented by introducing the glucose syrup through flow distributors which provide (initially) for uniform flow evenly across the column (cross-sectionally of the bed). Top to bottom mixing of the enzyme containing particles can be minimized by a uniform particle size.

Fortuitously, the variables that can be controlled and therefore predetermined, namely particle size, bed height and superficial velocity, have been discovered to fit the operating parameters of an expanded bed process to the isomerization of glucose syrups.

Since the intrinsic density of glucose isomerase cell mass particles will be in the range of 1.1–2.0 (not far above the syrup density). Particle size becomes crucial to expanded bed operations. The larger the particle size, the greater the settling velocity (following Stokes law). For isomerization under expanded bed conditions the particle range for the (wet) enzyme preparation should be in the range of 150–2,500 micrometers, with a preferred range of 0.4–1.5 millimeters. In addition minimum bed expansion constitutes the preferred mode of operation for plug flow reasons. Bed expansion of from 5–100%, and preferably 10–75%, is contemplated for practice of this invention (bed expansion being the height of the expanded bed versus the height of the wet bed under non-flow conditions). The superficial fluid flow rate should be adjusted to a level within the range of 0.5–15 meters per hour to stay within the above bed expansion range.

The fit of particle size, flow rate and bed height is subject to other complications. The unit activity of the cell mass enzyme particles (per gram) varies with particle size, larger particles being less active (on a unit activity basis) than small particles. In addition, activity of the enzyme preparation gradually declines from its initial value (with time and use) until in time the enzyme ultimately becomes completely deactivated. By reducing flow rate in relation to the decline in activity, the desired glucose to fructose conversion level can be maintained. When unit activity is below about 25% of initial activity, the enzyme is usually considered spent.

The expanded bed isomerization process is capable of operation with glucose syrups of any solids content level in the range of about 35–50%, and under the pH and temperature conditions most suitable for the enzyme, and is not dependent on how the cell mass particulate enzyme preparation is formed into uniform particles within the 150–2,500 micormeter size range. It may be noted that extrusion, as disclosed in both Ser. No. 501,292 and Pat. No. 3,821,086 followed by subdividing the extrudate is a preferred mode for forming a cell mass enzyme preparation into essentially uniformly sized particles. Particle size can be predetermined, and will depend on the extruder orifice.

DETAILED PRACTICE OF THE INVENTION

As has already been indicated a high degree of predictability for conducting expanded bed isomerization with a cell mass particulate enzyme preparation is provided by the following equation:

$$E = -130.606 - 40.962\,P - 0.502\,T + 4.470\,S + 11.084\,V$$

where
$E$ = % bed expansion
$P$ = particle size (mm)
$T$ = reactor temperature (° C.)
$S$ = percent solids (w/w) in substrate
$V$ = superficial linear velocity (meters/hour)

This equation has been derived from tests on the preparation made according to Example A herein, of an intrinsic density $d = 1.41$. Similar equations would result from particulate glucose isomerase cell mass enzyme preparations made from different microorganisms and or by different procedures.

The unit activity variable is not part of the above equation because bed height may be set in accordance with unit activity.

For understanding of the practice of the invention the above equation can be simplified by consideration of what happens when isomerizing at a typical temperature e.g. 65° C. and with the syrup at a typical solids level content, e.g. 40% solids (temperature and solids content are variables over which the process engineer has essentially no control). The equation then becomes:

$$E = -130.66 - 40.962\,P - 32.67 + 177.80 + 11.084\,V,\ \text{then}\ E = 17.074 - 40.962\,P + 11.084\,V$$

Basically the equation illustrates the extent that bed expansion depends upon particle size and superficial velocity of the syrup with larger particle size permitting higher fluid flow velocity.

For any particular installation the superficial velocity employed can be established by the production capabilities for the desired column. For example, an isomerization reactor 1.5 meters in diameter intended to be operated at an optimum flow rate of 5.4 meters per hour (to match the design capability of a plant converting starch to a glucose-fructose product) requires about 2,000 kilograms of enzyme, 1 millimeter in size (diameter) with an activity of about 190 IGIC u/gm for the desired conversion to fructose and the reactor will operate at a bed expansion of about 55% expansion. On the other hand, if the particle size of the glucose isomerase available were 1.5 millimeters, the bed expansion would be about 35%. However, since the unit activity of such enzyme may be expected to be lower (e.g. 165 IGIC units per gram), a greater weight of enzyme and deeper bed is required for the same conversion.

Conduct of an expanded bed isomerization reaction offers certain advantages compared to a fixed bed isomerization process. Catalyst can be added (i.e. deepen bed) to compensate for the decline in enzyme activity with time. The reaction operator can suspend enzyme particles in syrup and float enzyme into or out of the column, thereby facilitating charging and discharging of the reactor.

According to one preferred mode of operation, the reactor is charged with fresh enzyme, then employed under expanded bed flow rates for enzymatic isomerization with the flow rate gradually decreasing as necessary to maintain the desired fructose level, until the enzymatic activity has declined to too low a level, e.g. 25% of initial activity. Then isomerization is halted until the reactor has been discharged of spent enzyme and recharged with fresh enzyme.

Instead of lowering flow rate, the operator could add more (and fresh) enzyme to the bed, or combine lowered flow rate and addition of more enzyme. Still another alternative is to operate two expanded bed reactors in parallel when the enzyme is fresh, then in series after activity has declined to below about 50% of initial activity.

Extended studies comparing the operation of up flow expanded bed vs. a down flow fixed bed (with the same enzyme preparations), evidenced that the usual parameters for good isomerization conditions namely pH, operating temperature, and metal ion content (cobalt and magnesium) were the same for both modes. In addition enzyme half-life was about the same. However, uniformity in particle size was most important for expanded bed operation. Fine particles initially present in the enzyme charge are eluted out of an expanded bed almost immediately. To this extent the expanded bed mode evidenced an immediate (but small) loss of total enzyme activity.

As a whole expanded bed isomerization is believed to be superior to fixed bed operations, and operation in expanded bed systems is considered to constitute a superior procedure for glucose isomerization with cell mass particles.

The expanded bed system operates somewhat better when the cell mass particle includes 5–20% by wt thereof of finely divided evenly dispersed tabular aluminum oxide (for weighting purposes). The $Al_2O_3$ may for example be 325 mesh or finer. Tabular alumina is employed since high surface area is not desired. A preferred weighting range is 10–15% by wt of alumina.

Uniform dispersion of the alumina can be achieved by mixing in the alumina during the processing which converts the microorganism cells into the cell mass particulate form. For example in the preferred procedure suggested by Ser. No. 501,292, the alumina may be mixed in after reaction between glutaraldehyde and the cell homogenizate has thickened the homogenate enough to suspend the alumina particles.

The following table illustrates the affect weighting has upon cell mass particles prepared according to Example A herein.

| Extrudates 0.3 - 0.8 - mm | Unweighted | 12% $Al_2O_3$ |
|---|---|---|
| Initial activity | 150 IGIC/g | 130 |
| True density of dry enzyme | 1.4 g/ml | 1.5 |
| Wet bulk density | .270 kg/l | .32 |

The principal consequence of weighting is upon the fluid velocity required for bed expansion. For example to achieve 50% bed expansion with the particles described in the above table fluid velocity is 20% greater in the instance of the weighted particles.

EXAMPLE A

Preparation of the cell mass particles.

(1000 l of ) broth from a fermentation of a glucose isomerase containing B. coagulans, NRRL B 5656, were concentrated by centrifuging it at 10° C., to give 12 g dry weight per 100 ml concentrate.

20 l of the cell concentrate was homogenized by means of a Manton-Goulin homogenizer at 400 atm. to give a homogenate with about 95% of the activity in a soluble form. The homogenate was thereafter treated with a buffered 20% w/v acetic acid having a pH 3.5 to lower the concentrate's pH to 6.3. Then 800 ml of 50% w/w glutaraldehyde solution was added, the mixture thoroughly agitated, then left at 20° C. for 45' to gel. The gel thus formed was dispersed in 40 l deionized water, filtered on a filter press, and the cake ventilated in the filter press to remove some of the water, and the partially dried cake (11.6 kg) was extruded by means of an axial extruder with a screen of 1.0 mm, dried in a fluidized bed at an inlet temperature of 60° C., to give dry particles of cylindrical shape about 0.400 mm with very narrow size distribution, but a density which varied from batch to batch from about 0.26kg/l to 0.33kg/l in wet bulk density. Activity varied from batch to batch from about 100 IGIC to 300 IGIC; the particle sizes were changed by employing larger and smaller screens for the extrusion. Different batches of this (unweighted) product were employed in the Examples 1–4 which follow.

The same procedure was followed for preparing weighted particles, except that after the glutaraldehyde solution was added and the viscosity of the mixture had increased, 300 grams of 325 mesh tabular alumina was thoroughly intermixed into the mixture. Then the mixture was allowed to gel. The dried particles contained about 12% by wt of alumina, exhibited an absolute density of 1.5 g/ml.

EXAMPLE 1

(1) 35% (w/w) solution of glucose as the substrate
(2) Average particle size approximately 420 u M 281 gms of immobilized glucose isomerase (batch PPGL-11)

Activity; 220 IGIC u/gm
Wet bulk density; 0.26 Kg/l
Particle Size (Sieve Analysis)

| % greater than U.S. Standard Sieve #30 | ($>595\ \mu$) | 0.4 |
|---|---|---|
| % retained on U.S. Standard Sieve #40 | ($<595>420\ \mu$) | 58.1 |
| % retained on U.S. Standard Sieve #50 | ($<420>300\ \mu$) | 37.1 |
| % retained on U.S. Standard Sieve #100 | ($<300>150\ \mu$) | 4.2 |
| % less than #100 | ($<150\ \mu$) | 0.2 | were suspended in a 35% (w/w) (2.2M) solution of corn syrup solids (95% -D glucose; 5% oligomers, mostly maltose and isomaltose) that was $8 \times 10^{-3}$M in $MgSO_4.7H_2O$ and $3.6 \times 10^{-5}$M in $CoSO_4.7H_2O$. After gentle agitation for 1 hour, the suspension was transferred to a jacketed column, 2.59 cm inside diameter by 4.9 meters high, that was particlly filled with the same solution (substrate). The enzyme was supported by 80 mesh stainless steel screen covered by a 5 cm high layer of 1 mm diameter glass beads to act as a flow distributor. Fresh substrate was pumped through the column and a flow of 60° C. water was started through the column jacket. When the contents of the column had been heated to 60° C., the flow rate was adjusted so that the composition of the effluent was, on a solids basis, 42% fructose, 53% -D glucose and 5% higher oligomers. This resulted in the following conditions:

Volumetric Flow Rate: 30 ml/min
Superficial Linear Velocity: 3.41 meters/hour
Total Bed Height: 3.27 meters The flow of substrate was stopped and the bed allowed to settle. The settled bed height was measured and found to be 2.05 meters. The flow of substrate was restarted and column returned to the conditions described above. Based on these data the bed expansion was calculated as follows:

$$\% \text{ expansion} = \left[ \frac{\text{Total bed height}}{\text{Rest bed height}} \times 100 \right] - 100$$

$$\% \text{ expansion} = \left[ \frac{3.27 \text{ m}}{2.05 \text{ m}} \times 100 \right] - 100$$

$$\% \text{ expansion} = 59.5$$

The fructose content of the column effluent was determined periodically by high pressure liquid chromatography using the method described by Brobst et al. And, if the fructose content was less than 42% (solids basis)

the flow rate through the column was decreased to a level that would yield the desired fructose level.

The total bed height was measured after each adjustment in the flow rate and the % expansion of the enzyme bed was calculated. Typical values are shown in Table 1:

TABLE 1

| Total Operating Time (hours) | Enzyme Activity | Vol. flow Rate ml/min | SLV M/hr. | Percent Expansion |
|---|---|---|---|---|
| 0 | 220 | 31.8 | 3.6 | 62 |
| 264 | 220 | 31.8 | 3.6 | 62 |
| 360 | 193 | 27.9 | 3.2 | 53 |
| 600 | 118 | 17.0 | 1.9 | 34 |
| 840 | 108 | 15.1 | 1.7 | 32 |
| 1440 | 70 | 10.3 | 1.2 | 18 |

EXAMPLE 2

45% (w/w) corn syrup solids (95% alpha-D glucose, 5% higher oligomers, mostly maltose and isomaltose). Average particle size approximately 400 $u$ M. 260 gms of glucose isomerase (batch PPGL-13) having the following properties:

Activity; 151 IGIC u/gm
Wet bulk density; 0.33 Kg/l
Particle Size (Sieve Analysis)

| | | |
|---|---|---|
| % greater than U.S. Standard Sieve #30 | (>595 μ M) | 0.0 |
| % retained on U.S. Standard Sieve #40 | (<595 >420) | 75.0 |
| % retained on U.S. Standard Sieve #80 | (<420 >177) | 24.8 |
| % retained on U.S. Standard Sieve #100 | | 0.2 | were suspended in a 45% (w/w) (3.0 M) solution of corn syrup solids (95% -D glucose; 5% oligomers, mostly maltose and isomaltose) that was $4 \times 10^{-3}$M with respect to $MgSO_4.7H_2O$. After gentle agitation for 1 hour, the suspension was transferred to a jacketed column 2.13 cm inside diameter by 4.27 M high that was partially filled with the same 45% (w/w) solution of corn syrup solids (substrate).

Fresh substrate was pumped through the column and a flow of 60° C. water was started through the column jacket. When the contents of the column had reached 60° C., the flow rate of substrate was adjusted so that the column effluent contained 42% by weight (solids basis) fructose. This level of fructose was obtained at a flow rate of 15.8 ml/min. At this flow rate, the superficial linear velocity is:

$$\frac{15.8 \text{ ml/min} \times 60 \text{ min}}{3.56 \text{ cm}^2 \times 100} = 2.66 \text{ m/hour}$$

where 3.56 cm² is the cross sectional area of the column. The bed height at this flow rate and the settled bed height were measured as in Example 1 and found to be 3.36 M and 2.21 M respectively. The % expansion was calculated as in Example 1 and found to be 52%. As in Example 1, the fructose level in column effluent was determined periodically and the flow rate was decreased as necessary to maintain a constant fructose level. The flow rate, activity, superficial linear velocity and % bed expansion are shown as functions of operating time in Table 2:

TABLE 2

| Operating Time Hours | Enzyme Activity | Vol. Flow Rate (ml/min) | SLV M/hr. | Percent Expansion |
|---|---|---|---|---|
| 0 | 153 | 15.8 | 2.66 | 52 |
| 72 | 153 | 15.8 | 2.66 | 52 |
| 168 | 133 | 13.3 | 2.25 | 43 |
| 288 | 108 | 11.2 | 1.88 | 34 |
| 408 | 87 | 8.8 | 1.50 | 26 |
| 648 | 70 | 7.1 | 1.2 | 19 |
| 1032 | 40 | 4.0 | 0.7 | approx. 8 |

EXAMPLE 3

(1) 35% (w/w) solution of glucose as the substrate
(2) Average particle size approximately 190 $u$ M
62 gms of immobilized glucose isomerase (batch PPGL-04) having the following properties:
Activity; 94 IGIC u/gm
Wet bulk density; 0.31 Kg/l
Particle Size (Sieve Analysis)

| | | |
|---|---|---|
| % greater than U.S. Standard Sieve #50 | (<297 μ) | 2.0 |
| % retained on U.S. Standard Sieve #70 | (>297 <210) | 40 |
| % retained on U.S. Standard Sieve #100 | (>210 <150) | 58 | was treated as described in Example 1 except that a jacketed column, 1.7 cm diameter by 1.22 M high was used in this test. After temperature equilibration the flow rate was adjusted so that the column effluent contained 42% by weight fructose (solids basis). This composition was maintained by periodically adjusting the flow rate of substrate through the column. The enzyme activity, flow rates, SLV and % bed expansion were determined as described above and are shown in Table III. The rest bed height was 0.88 M

TABLE 3

| Operating Time Hours | Enzyme Activity | Vol. Flow Rate (ml/min) | SLV M/hr. | Percent Expansion |
|---|---|---|---|---|
| 24 | 94 | 2.78 | 0.73 | 9 |
| 240 | 94 | 2.78 | 0.73 | 9 |
| 480 | 72 | 2.10 | 0.55 | less than 5 |
| 1080 | 41 | 1.37 | 0.36 | less than 5 |

EXAMPLE 4

(1) 45% (w/w) solution of glucose as substrate
(2) Average particle size approximately 800 $u$ M
120 gms of immobilized glucose isomerase (batch ITA 780) having the following properties:
Activity; 215 IGIC u/gm
Wet bulk density; 0.27 Kg/l
Particle Size (Sieve Analysis)

| | | |
|---|---|---|
| % greater than U.S. Standard Sieve #14 | (<1.41 mm) | 0 |
| % retained on U.S. Standard Sieve #20 | (>1.41<.841 mm) | 25 |
| % retained on U.S. Standard Sieve #30 | (>841<595 μ) | 67.5 |
| % retained on U.S. Standard Sieve #40 | (>595<420 μ) | 7 |
| % less than U.S. Standard Sieve #40 | (>420 μ) | 0.5 | was transferred to a jacketed column 2.13 cm inside diameter by 2.13 M high trhough which an aqueous solution, 0.1 M in $NaHCO_3$, $8 \times 10^{-3}$M in Mg ion (as $MgSO_4.7H_2O$), $3.6 \times 10^{-5}$ in Co ions ($CoSO_4.7H_2O$) and $8 \times 10^{-3}$M in $Na_2SO_3$, pH of solution 7.5 was flowing at a superficial linear velocity of 10 meters per hour which is sufficient to expand the enzyme particles. The flow of this solution was maintained at this rate for 2 hours. At this point the solution was changed to one that was 0.1 M in NaHCO$_3$, 8 × 10$^{-3}$M in Mg ions and 8 × 10$^{-3}$M in Na$_2$SO$_3$. This flow was continued for 2 hours. At the end of this time period a solution of 45% w/w corn syrup solids (95% glucose, 5% oligomers on a solids basis) containing 8 × 10$^{-3}$M Mg ions and 6 × 10$^{-4}$M SO$_3$ = ions as Na$_2$SO$_3$, preheated to 60° C. was introduced into the bottom of the column at a volumetric flow rate of 15 ml/minute (equal to an SLV of 2.5 M/hr). When glucose appeared in the column effluent, a flow of 60° C. water was introduced into the column jacket. After temperature equilibrium was attained in the column, the flow rate was adjusted so that the column effluent contained 42% fructose (solids basis). After 5 column volumes had passed through the column, the effluent was sampled and analyzed for fructose. Then the flow was stopped and the rest height of the bed was measured. The results of these measurements are listed in Table 4.

TABLE 4

| | | |
|---|---|---|
| % Fructose in Column Effluent (solids basis) | 42.7 | % |
| Volumetric flow rate | 14.3 | ml/min |
| SLV | 2.41 | M/hr. |
| Bed Height | 1.66 | M |
| Rest bed height | 1.25 | M |
| % bed expansion | 33.0 | % |

The substrate flow was restarted and the column was returned to the conditions shown in Table 4. Flow was continued and, as described in previous examples, adjusted periodically based on assay of the fructose, to maintain the fructose level in the effluent at 42% on a solids basis. As in the previous examples, the bed height was measured after each change in the flow rate and the % bed expansion was calculated. Typical values are listed in Table 5.

TABLE 5

| Total Operating Time (hours) | Enzyme Activity | Vol. Flow Rate (ml/min) | SLV M/hr. | Percent Expansion |
|---|---|---|---|---|
| 24 | 258 | 14.3 | 2.41 | 33 |
| 240 | 258 | 14.3 | 2.41 | 33 |
| 480 | 145 | 9.3 | 1.56 | 19 |
| 720 | 140 | 9.0 | 1.51 | 17 |

EXAMPLE 5

A comparative study was carried out using weighted and unweighted particles prepared as described in Example A, extruding through a 0.8 mm screen. The unweighted product density was 1.4 g/ml, the weighted product was 1.51 g/ml. Activity of unweighted particles was 247 GINU (about 90 IGIC), and weighted particle was 225 GINU (about 85 IGIC).

In a test column operated with 45% glucose at 60° C. and varying superficial linear velocity. The following results were obtained.

TABLE 6

| SLV | Bed Expansion | |
|---|---|---|
| m/hr. | Unweighted | Weighted |
| 2 | 24% | 12.5% |
| 4 | 58% | 37% |

TABLE 6-continued

| SLV | Bed Expansion | |
|---|---|---|
| m/hr. | Unweighted | Weighted |
| 6 | 84% | 61% |

EXAMPLE 6

A total of 135 gms of weighted enzyme (Batch I —70103) — Activity 208IGIC true density 1.51 g/ml. wt. bulk density 0.29 Kg/l, 12% Al$_2$O$_3$ by wt. made according to the method of Example A was pretreated and otherwise handled according to the method of Example 4, except that a 35% glucose syrup constituted the substrate (pH 8.5, T°-65°). Due to the mis-match of column to available enzyme the conversion of glucose to fructose was held to 32% dsb. (A column twice as high would have been required for 40% conversion).

The sieve analysis was as follows:
% greater than 0.84 mm; 4.5%
% retained on 0.595 mm (30 Mesh); 85.8%
% retained on 0.420 mm (40 Mesh); 9.5%

Over the life of the enzyme, typical values obtained are listed in Table 7.

TABLE 7

| Total Operating Time (hours) | Enzyme Activity | Vol. Flow Rate ml/min | SLV M/hr. | Percent Expansion |
|---|---|---|---|---|
| 24 | 261 | 52 | 8.0 | 42 |
| 240 | 210 | 42 | 6.5 | 32 |
| 480 | 170 | 33 | 5.0 | 21 |
| 720 | 136 | 27 | 4.1 | 14 |
| 960 | 109 | 21 | 3.2 | 6 |

What is claimed is:

1. A process utilizing expanded bed isomerization to convert glucose syrup to a glucose-fructose mixture containing at least 40% fructose by weight of the glucose-fructose content which comprises passing a 30–55% w/w of glucose syrup at isomerizing temperature and pH conditions up through at least one bed of a cell mass particulate form glucose isomerase preparation having uniform size in the range of 150–2,500 micrometers at a superficial linear velocity for the syrup of 0.5–15 meters an hour, said velocity and particle size being related in an inverse relation to create a bed expansion within the range of 5–100% and plug flow by the syrup through the bed, the bed depth being sufficient to achieve the aforementioned at least 40% fructose content.

2. The process of claim 1 wherein the life of the bed is extended by intermittently or continuously adding fresh enzyme.

3. The process of claim 1 wherein the activity of the glucose isomerase preparation exceeds about 100 IGIC u/gram.

4. The process of claim 1 wherein isomerization is carried out until the unit activity of the enzyme has declined to about 25% of its initial activity at an ever decreasing syrup flow, the flow rate decreasing as enzyme activity decreases.

5. The process of claim 1 wherein the cell mass particulate form glucose isomerase preparation contains uniformly dispersed therein finely divided aluminum oxide as from 5–20% by weight thereof.

* * * * *